(12) United States Patent
Fink et al.

(10) Patent No.: US 8,386,026 B2
(45) Date of Patent: Feb. 26, 2013

(54) SYSTEM AND METHOD FOR ACQUIRING AND DISPLAYING ABDOMINAL EMG SIGNALS

(75) Inventors: Rainer J. Fink, College Station, TX (US); Robert Garfield, Goodyear, AZ (US); Jack N. McCrary, Houston, TX (US)

(73) Assignee: Reproductive Research Technologies, L.P., Houston, TX (US)

( * ) Notice: Subject to any disclaimer, the term of this patent is extended or adjusted under 35 U.S.C. 154(b) by 0 days.

(21) Appl. No.: 12/758,596

(22) Filed: Apr. 12, 2010

(65) Prior Publication Data

US 2011/0251512 A1    Oct. 13, 2011

(51) Int. Cl.
*A61B 5/00*    (2006.01)
(52) U.S. Cl. ........................................ 600/546
(58) Field of Classification Search ................ 600/546, 600/547, 588
See application file for complete search history.

(56) References Cited

U.S. PATENT DOCUMENTS

| | | | |
|---|---|---|---|
| 3,703,168 A | 11/1972 | Frink | |
| 4,256,118 A | 3/1981 | Nagel | |
| 4,299,234 A | 11/1981 | Epstein et al. | |
| 4,308,873 A | 1/1982 | Maynard | |
| 4,577,640 A * | 3/1986 | Hofmeister | 600/551 |
| 4,738,268 A | 4/1988 | Kipnis | |
| 4,781,200 A | 11/1988 | Baker | |
| 4,945,917 A | 8/1990 | Akselrod et al. | |
| 4,967,761 A | 11/1990 | Nathanielsz | |
| 5,042,499 A | 8/1991 | Frank et al. | |
| 5,205,296 A * | 4/1993 | Dukes et al. | 600/588 |
| 5,209,237 A | 5/1993 | Rosenthal | |
| 5,301,680 A | 4/1994 | Rosenberg | |
| 5,372,139 A | 12/1994 | Holls et al. | |
| 5,397,344 A | 3/1995 | Garfield et al. | |
| 5,400,799 A | 3/1995 | Yoches | |
| 5,447,526 A | 9/1995 | Karsdon | |
| 5,483,970 A | 1/1996 | Rosenberg | |
| 5,546,953 A | 8/1996 | Garfield | |
| 5,581,369 A | 12/1996 | Righter et al. | |
| 5,623,939 A | 4/1997 | Garfield | |
| 5,776,073 A | 7/1998 | Garfield et al. | |
| 5,785,664 A | 7/1998 | Rosenberg | |
| 5,791,342 A | 8/1998 | Woodard | |
| 5,964,789 A | 10/1999 | Karsdon | |

(Continued)

OTHER PUBLICATIONS

Demianczuk et al., Am. J. Obstet. Gynecol., vol. 149, No. 5, pp. 484-491 pp. 485-491 (Jul. 1, 1984).

(Continued)

*Primary Examiner* — Max Hindenburg
(74) *Attorney, Agent, or Firm* — Hulsey, P.C.; Loren T. Smith; William N. Hulsey, III (57) ABSTRACT

A system and method for acquiring and processing abdominal EMG signals from a maternal patient to indicate when a maternal patient should push to progress the labor toward delivery. Raw abdominal EMG signals are acquired and processed in a central unit designed to isolate the patient and any internal circuitry from electrical shock. The central unit has a circuit board that amplifies and filters the EMG signal, then transmits the signal to an A/D converter, after which the digitized signal is transmitted to a computer for further processing and subsequent display of a signal representative of abdominal activity. The system may also acquire and process uterine EMG signals that can be evaluated in conjunction with the abdominal EMG signals.

20 Claims, 7 Drawing Sheets

U.S. PATENT DOCUMENTS

| | | | |
|---|---|---|---|
| 5,991,649 | A | 11/1999 | Garfield et al. |
| 6,134,466 | A | 10/2000 | Rosenberg |
| 6,290,657 | B1 | 9/2001 | Adams |
| 6,421,558 | B1 | 7/2002 | Huey et al. |
| 6,748,263 | B2 * | 6/2004 | Griffiths et al. .............. 600/544 |
| 6,816,744 | B2 | 11/2004 | Garfield et al. |
| 6,823,211 | B2 | 11/2004 | Simpson et al. |
| 6,879,858 | B1 | 4/2005 | Adams |
| 7,333,850 | B2 | 2/2008 | Marossero et al. |
| 7,447,542 | B2 * | 11/2008 | Calderon et al. .............. 600/546 |
| 7,468,032 | B2 | 12/2008 | Stahmann et al. |
| 7,532,923 | B1 | 5/2009 | Hayes-Gill et al. |
| 7,616,980 | B2 | 11/2009 | Meyer |
| 7,689,275 | B2 | 3/2010 | Blomberg et al. |
| 7,758,522 | B2 | 7/2010 | Pandit |
| 7,828,753 | B2 | 11/2010 | Euiano et al. |
| 7,925,323 | B2 | 4/2011 | Meyer |
| 2002/0193670 | A1* | 12/2002 | Garfield et al. .............. 600/304 |
| 2006/0189882 | A1* | 8/2006 | Thomas .................. 600/546 |
| 2007/0213627 | A1 | 9/2007 | James et al. |
| 2008/0275316 | A1 | 11/2008 | Fink et al. |
| 2009/0036787 | A1 | 2/2009 | James et al. |
| 2009/0192396 | A1 | 7/2009 | Hayes-Gill et al. |

OTHER PUBLICATIONS

Devedeux, Marque, Duchene, Germain, Mansour, "Uterine Electromyography: A Critical Review," Am. J. Obstet. Gynecol. 169:1636-1653, 1993.

Dill and Maiden, "The Electrical Potentials of the Human Uterus in Labor," Am. J. Obstet. Gynecol. 52:735-745, 1946.

Steer, "The Electrical activity of the Human Uterus in Normal and Abnormal Labor," Am. J. Obstet. Gynecol. 68:867-890, 1954.

Halliday and Heyns, "Uterine Activity and Electrical Response," J. Obstet. Gynaec. Brit. Emp. 62:155-161, 1955.

Hon and Davis, "Cutaneous and Uterine Electrical Potentials in Labor—an Experiment," Obstet. Gynec. 12:47-53, 1958.

Margue et al., "Uterine EHG Processing for Obstetrical Monitoring," IEEE Transactions on Biomedical Engineering, BME-33(12):1182-1186, Dec. 1986.

Larks SD, Dasgupta K.; "Wave Forms of the Electrohysterogram in Pregnancy and Labor," Am J Obstet Gynecol, May 1958; 75(5):1069-78.

Lucovnik M, Maner WL, Chambliss LR, Blumrick R, Balducci J, Novak-Antolic Z, Garfield RE. "Noninvasive uterine electromyography for prediction of preterm delivery," Am J Obstet Gynecol. Mar. 2011; 204(3):228.e1-10; Epub Dec. 8, 2010.

Garfield RE, Maner WL, Mackay LB, Schlembach D, Saade GR.; "Comparing uterine electromyography activity of antepartum patients versus term labor patients," Am J Obstet Gynecol. Jul. 2005;193(1):23-9.

* cited by examiner

SYSTEM AND METHOD FOR ACQUIRING AND DISPLAYING ABDOMINAL EMG SIGNALS

BACKGROUND

The progress of a normal maternal delivery is generally driven by two types of labor forces: a primary force produced by the involuntary contractions of the uterine muscles, and a secondary force produced by the increase of intra-abdominal pressure through voluntary contractions of the abdominal muscles and diaphragm. During the labor process, these two forces are designed to work concurrently to provide an increase in intrauterine pressure that supplies the critical expulsion force on the fetus. Ideally, the maternal patient will attempt to voluntarily contract her abdominal muscles to directly coincide with the forces of the involuntary uterine contractions or the instructions provided by a healthcare provider.

However, through the implementation of the commonly-employed epidural anesthesia, the overall ability of the maternal patient to manage and direct the secondary force can be reduced significantly. By blocking the transmission of signals through nerves in the spinal cord, the epidural not only causes a loss of pain for the maternal patient, but also results in the overall loss of muscular sensation, especially sensation to the abdominal muscles used in the birthing process. Thus, following an epidural, the maternal patient often cannot tell how much force is being exerted through the abdominal muscles when "pushing," or whether she is actually pushing at all. Indeed, in some cases, the maternal patient can have difficulty isolating and pushing with the correct muscles. In the worst case, the patient voluntary pushing may be completely out of phase from the uterine contraction, thus counteracting the desired progression of labor.

What is needed, therefore, is a system and method that indicates when a maternal patient should push and reports to the attending physician and patient whether the push was an "effective push," or a push that verifiably progressed the labor toward delivery.

SUMMARY

Embodiments of the disclosure may provide a system for processing abdominal EMG signals. The system may include a signal processing module having an internal processing circuit, and at least one pair of electrodes communicably coupled to the signal processing module and configured to acquire and transmit a raw abdominal EMG signal from a patient to the internal processing circuit where the raw abdominal EMG signal is for amplified and filtered to a frequency band between about 20 Hz and about 150 Hz, thereby obtaining a processed abdominal EMG signal. The system may further include an analog to digital converter operatively coupled to the processing circuit and configured to convert the processed abdominal EMG signal into a digital abdominal EMG signal, and a computer communicably coupled to the signal processing module and configured to receive and process the digital abdominal EMG signal into a viewable signal representative of abdominal activity. Using the computer, the intensity of abdominal activity can be evaluated alongside a uterine EMG signal.

Embodiments of the disclosure may further provide a method of processing abdominal EMG signals. The method may include obtaining a raw analog abdominal EMG signal from a pair of electrodes applied to a maternal abdomen of a patient, and processing the raw analog abdominal EMG signal in a signal processing module by amplifying and filtering the raw analog abdominal EMG signal to a frequency band between about 20 Hz and about 150 Hz, thereby obtaining a processed analog signal. The method may further include converting the processed analog signal to a digital abdominal EMG signal, and converting the digital abdominal EMG signal into a signal representative of abdominal activity using a computer communicably coupled to the signal processing module.

Embodiments of the disclosure may further provide a computer program embodied on a computer-readable medium, that when executed by a processor, is configured to control a method for processing abdominal EMG signals from a patient. The computer program may include instructions for obtaining a raw analog abdominal EMG signal from at least one pair of electrodes coupled to a maternal abdomen of a patient, and processing the raw analog abdominal EMG signal in a signal processing module to amplify and filter the raw analog abdominal EMG signal to a frequency band between about 20 Hz and about 150 Hz to obtain an amplified and filtered analog signal. The computer program may include further instructions for converting the amplified and filtered analog signal to a digital abdominal EMG signal, transmitting the digital abdominal EMG signal to a computer, and processing the digital abdominal EMG signal in the computer to obtain a signal representative of abdominal activity. The computer program may also include instructions for displaying the signal representative of abdominal activity on a monitor communicably coupled to the computer, whereby an intensity of abdominal activity can be evaluated alongside a uterine EMG signal.

BRIEF DESCRIPTION OF THE DRAWINGS

The disclosure is best understood from the following detailed description when read with the accompanying Figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure may repeat reference numerals and/or letters in the various exemplary embodiments and across the Figures provided herein. This repetition is for the purpose of simplicity and clarity and does not in itself dictate a relationship between the various exemplary embodiments and/or configurations discussed in the various Figures. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Finally, the exemplary embodiments presented below may be combined in any combination of ways, i.e., any element from one exemplary embodiment may be used in any other exemplary embodiment, without departing from the scope of the disclosure.

Additionally, certain terms are used throughout the following descriptions and claims to refer to particular components. As one skilled in the art will appreciate, various entities may refer to the same component by different names, and as such, the naming convention for the elements described herein is not intended to limit the scope of the invention, unless otherwise specifically defined herein. Further, the naming convention used herein is not intended to distinguish between components that differ in name but not function. Further, in the following discussion and in the claims, the terms "including" and "comprising" are used in an open-ended fashion, and thus should be interpreted to mean "including, but not limited to." All numerical values in this disclosure may be exact or approximate values unless otherwise specifically stated. Accordingly, various embodiments of the disclosure may deviate from the numbers, values, and ranges disclosed herein without departing from the intended scope. Furthermore, as it is used in the claims or specification, the term "or" is intended to encompass both exclusive and inclusive cases, i.e., "A or B" is intended to be synonymous with "at least one of A and B," unless otherwise expressly specified herein.

Figure 1:
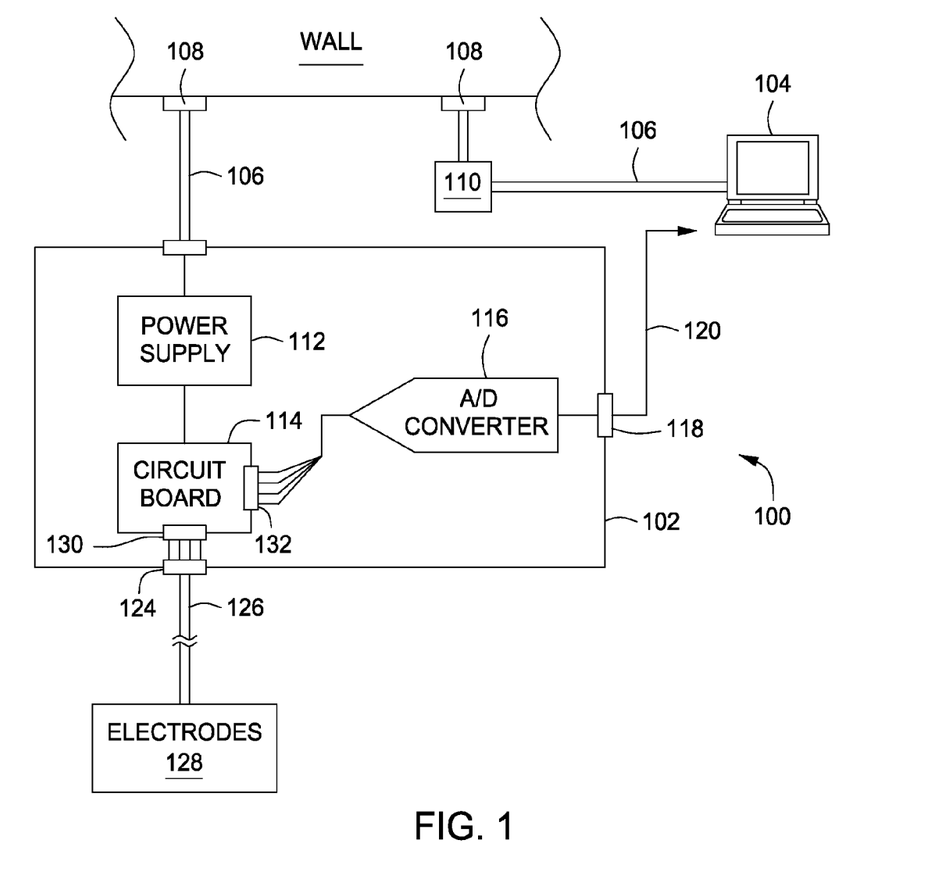
FIG. 1 illustrates a schematic of the abdominal EMG signal system according to one or more embodiments of the disclosure.

Referring to FIG. 1, illustrated is a system 100 for acquiring and processing secondary labor forces, or abdominal smooth muscle electromyography (EMG) signals, for observation during and after the labor process. The system 100 may also be capable of simultaneously acquiring and processing primary labor forces, or uterine EMG signals, to allow a physician to detect the onset of a uterine contraction and direct the maternal patient to supplement the contraction by pushing with the abdominal muscles.

Abdominal EMG signals can be detected by measuring the electrophysiological activity in the abdominal muscle fiber. For instance, when a motor unit fires, an action potential is carried down the motor neuron to the muscle, thereby eliciting an action potential in all of the innervated muscle fibers of that particular motor unit. When electrodes are placed on the maternal abdomen, they may measure the action potential created by a muscle contraction, thereby resulting in a "raw" abdominal EMG signal.

The system 100 may include a signal processing module 102 communicably coupled to a computer 104. The signal processing module 102 and the computer 104 may each include hardware. The hardware may include at least processor-capable platforms, such as client-machines (also known as personal computers or servers) and hand-held processing devices (such as smart phones, personal digital assistants (PDAs), or personal computing devices (PCDs), for example). Further, hardware may include any physical device that is capable of storing machine-readable instructions, such as memory or other data storage devices. Other forms of hardware include hardware sub-systems, including transfer devices such as modems, modem cards, ports, and port cards. In short, the computer 104 may include any other micro processing device, as is known in the art. The computer 104 may include a monitor for displaying processed abdominal EMG signals for evaluation.

The computer 104 may also include software for executing machine-readable instructions to produce a desired result. In at least one embodiment, the software may include an executable software program created in commercially-available LABVIEW®. In an exemplary embodiment, the computer 104 may include, without limitation, a desktop computer, laptop computer, or a mobile computing device. Moreover, the computer 104 may include a CPU and memory (not shown), and may also include an operating system ("OS") that controls the operation of the computer 104. The OS may be supported by MICROSOFT® Windows®, but in other embodiments, the OS may be any kind of operating system, including without limitation any version of the LINUX® OS, any version of the UNIX® OS, or any other conventional OS as is known in the art.

Both the signal processing module 102 and the computer 104 may be powered via a medical-grade power cord 106 that may be connected to any typical wall outlet 108 conveying operating power, which may be 120 volts for U.S.-based applications, but may be different in foreign-based applications. As can be appreciated, the system 100 may also be configured to operate on varying voltage systems present in foreign countries. For the computer 104, however, the power cord 106 may include an interim, medical-grade power brick 110 configured to reduce or eliminate leakage current originating at the wall outlet 108 that may potentially dissipate through the internal circuitry of the system 100 or a patient.

The signal processing module 102 may house a power supply module 112, a circuit board module 114, and an analog to digital ("A/D") converter 116. The power supply module 112 may be configured to supply power for the signal processing module 102. In particular, the power supply module 112 may receive operating power of 120V-60 Hz for the U.S. from the wall outlet 108 and convert that into a 12 volt direct current to be supplied to the circuit board module 114. In alternative embodiments, the power supply module 112 may be configured to receive various types of power, for example, DC current from a battery or power sources available in foreign countries. As will be described in more detail below, the circuit board 114 may be an electronic circuit and be configured to receive, amplify, and filter incoming abdominal EMG signals.

The A/D converter 116 may digitize the incoming analog abdominal EMG signals into a viewable digital signal transmittable to the computer 104 for display as a signal representative of abdominal activity. Specifically, the A/D converter 116 may be communicably coupled to an external USB port 118 located on the body of the signal processing module 102. In an exemplary embodiment, the USB port 118 may include a commercially-available USB 6008, available through NATIONAL INSTRUMENTS®. A double-ended USB connection cable 120 may be utilized to communicably couple the USB port 118 to the computer 104. As can be appreciated, however, the disclosure also contemplates alternative embodiments where the USB port 118 may be replaced with a wireless adapter and signal transmitter to wirelessly transmit the processed abdominal EMG data directly to a receiver located on the computer 104.

The signal processing module 102 may also include an EMG communication port 124, which may be communicably coupled to at least one pair of electrodes 128 and a patient ground electrode via an EMG channel 126. Although only one EMG channel 126 is illustrated, the disclosure fully contemplates using multiple EMG channels 126, where each EMG channel 126 is communicably coupled to a separate pair of electrodes 128. In an exemplary embodiment, there may be four or more separate EMG channels 126 entering the EMG communication port 124.

Through the electrodes 128, physicians may acquire and process raw abdominal EMG signals. Specifically, the electrodes 128 may be configured to measure the differential muscle potential across the area between a pair of electrodes 128 and reference that potential to patient ground. Once the muscle potential is acquired, the raw abdominal EMG signal may then be routed to an input 130 for processing within the circuit board 114, as will be described below.

After processing within the circuit board 114, the processed abdominal EMG signal may be directed out of the circuit board 114, through an output 132, and to the A/D converter 116 where the analog abdominal EMG signal may be digitized for display on the computer 104 as a signal representative of abdominal activity in the patient. The digitized abdominal EMG signal may be transmitted to the computer 104 via the USB port 118 and double-ended USB connection cable 120, as described above. However, alternative embodiments contemplate transmitting the data wirelessly to the computer 104 via a wireless adapter and signal transmitter/receiver combination (not shown).

According to at least one embodiment, the processed abdominal EMG signal (i.e., the signal representative of abdominal activity) may be displayed on the computer 104, stored in a memory (not shown) for future reference, transmitted, or printed for evaluation by an attending physician. The abdominal EMG signal representative of abdominal activity may quantify, among other things, the general intensity of the secondary force (i.e., the voluntary contraction of the abdominal muscles) by the maternal patient. In instances where epidural anesthesia is employed and general loss of sensitivity to abdominal muscles may occur, this may prove advantageous in order to assess whether the maternal patient is pushing hard enough, or pushing at all, to supplement the primary force (i.e., the uterine contractions) and thereby advance the delivery.

Figure 2:
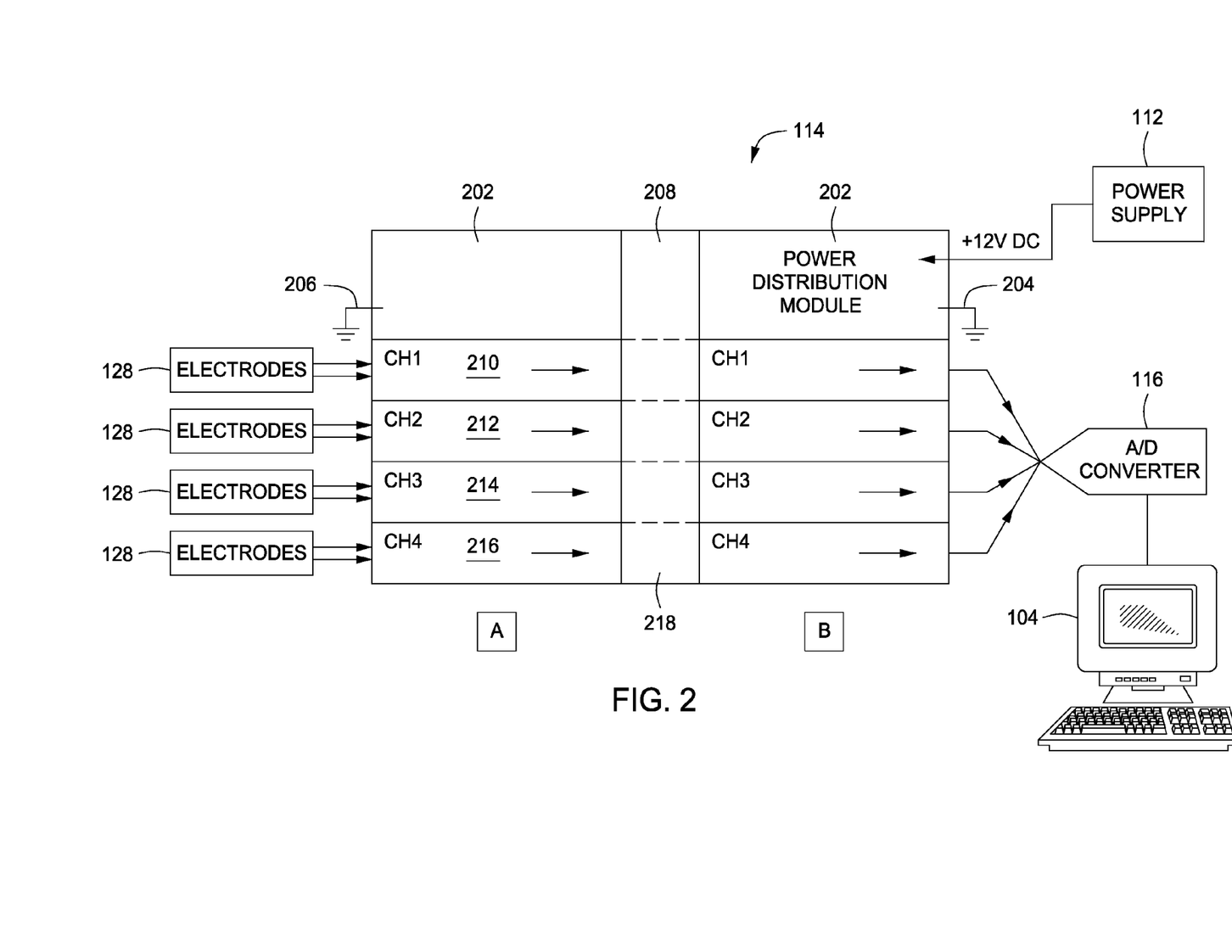
FIG. 2 illustrates a schematic of the circuit board illustrated in FIG. 1.

Referring now to FIG. 2, illustrated is an exemplary embodiment of the circuit board 114 located in the signal processing module 102, as described in FIG. 1. The circuit board 114 may include a patient side A, and a wall side B. As explained above, the circuit board 114 may receive a 12V direct current from the power supply module 112. In particular, the power supply module 112 may be communicably coupled to a power distribution module 202 located within the circuit board 114, wherein the power distribution module 202 may be configured to supply varying amounts of voltage to the internal circuitry of the circuit board 114. The power distribution module 202 may include a wall ground 204 and a patient ground 206, designed to not only protect the patient from stray leakage current but also to protect the internal circuitry from overload, as described below.

To help facilitate electrical shock protection for both the patient and the circuitry, the circuit board 114 may include an isolation DC-DC converter 208, or a transformer that separates the patient side A from the wall side B. In exemplary operation, the isolation DC-DC converter 208 may be configured to isolate power signals, thereby preventing stray charges from crossing over from one side and causing damage on the opposite side. In at least one embodiment, the isolation DC-DC converter 208 may include a commercially-available PWR1300 unregulated DC-DC converter.

As illustrated in FIG. 2, the circuit board 114 may be divided into a series of channels 210, 212, 214, 216. In the exemplary illustrated embodiment, four channels 210, 212, 214, 216 are indicated, labeled as CH1, CH2, CH3, and CH4, respectively, and may extend across both patient side A and wall side B. Each channel 210, 212, 214, 216 may be communicably coupled to a separate pair of electrodes 128, as described above. Once the raw abdominal EMG signal is obtained by the electrodes 128, the differential signal may then be delivered to each respective channel 210, 212, 214, 216 for processing and subsequent display of a signal representative of abdominal activity.

Although four separate channels 210, 212, 214, 216 are herein disclosed, alternative embodiments may include more or less than four. In fact, suitable results may be achieved by employing a single-channel configuration. However, since inaccurate EMG signals can often result from poor skin impedance or misplacement of the electrodes 128, a plurality of channels 210, 212, 214, 216 may afford the physician with a plurality of opportunities to acquire an accurate abdominal EMG signal. Furthermore, each channel 210, 212, 214, 216 may be separately-viewable on the computer 104 (FIG. 1) after signal processing has taken place.

Similar to the power distribution module 202, as a precautionary measure the channels 210, 212, 214, 216 on patient side A can be isolated from their counterpart channels 210, 212, 214, 216 on wall side B by a linear optocoupler 218. In an exemplary embodiment, the linear optocoupler 218 may include a commercially-available 1L300 optocoupler, available through VISHAY SEMICONDUCTORS®, or other similar devices. As can be appreciated to those skilled in the art, the linear optocoupler 218 may serve to avert potential electrical damage to the circuit 114 and the patient (not shown), as leakage current will be prohibited from being transmitted from one side A to the other side B, or vice versa.

In exemplary operation, the linear optocoupler 218 may be configured to receive a partially processed EMG signal from the patient side A and create an optical light signal that transmits across the linear optocoupler 218 to the wall side B. To be able to optically transmit a signal across the linear optocoupler 218 from the patient side A to the wall side B, the incoming raw abdominal EMG signal must first be amplified and filtered, as will be described in detail below. At the wall side B, the optical signal may then be converted back into an electrical signal and then undergo final amplification and filtration processes, as will also be described below. After final amplification and filtration on the wall side B, the processed abdominal EMG signal may then be transmitted to the A/D converter 116 where the signal can be digitized for display on the computer 104 (FIG. 1).

Referring now to FIGS. 3-6, illustrated are exemplary schematic diagrams for an embodiment of the power distribution module 202, as described above with reference to FIG. 2. To provide clean and safe power to the circuitry of the circuit board 114, the power distribution module 202 may be configured to filter and amplify the incoming power signals several times. As can be appreciated, clean power is desired so as to eliminate external noises introduced into the system via the power supply 112 (FIG. 1), thereby allowing the electrodes 128 to accurately register signals created only by the patient.

Figure 3:
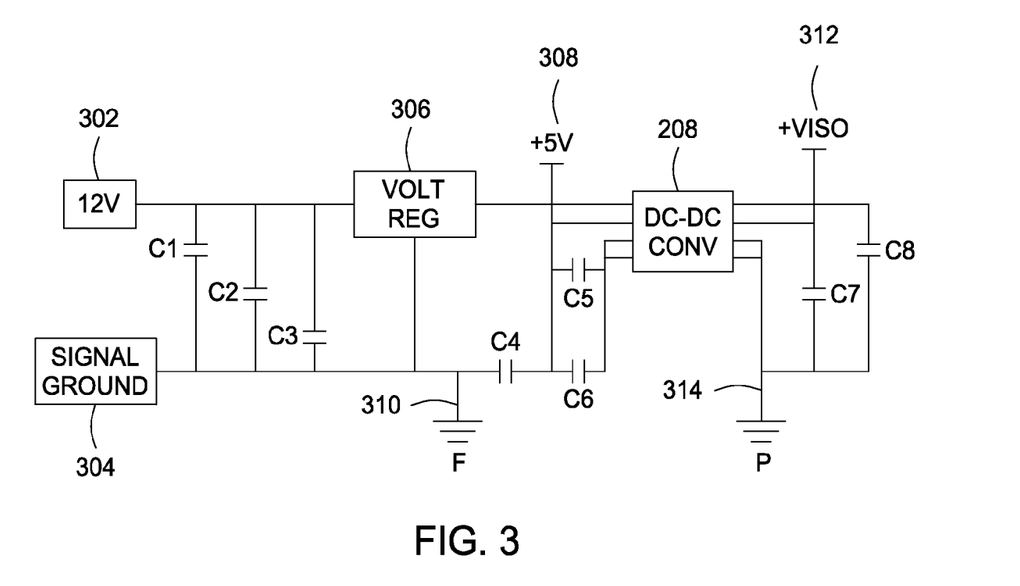
FIG. 3 illustrates a schematic diagram of a portion of the power distribution module disclosed in FIG. 2.

With reference to FIG. 3, the power distribution module 202 may include a 12V input power signal 302 and a signal input ground 304, both derived from the power supply 112 disclosed in FIG. 1. Although the 12V input power signal 302 was previously converted into a clean, medical-grade power via the power supply module 112, the power distribution module 202 may be designed to further clean the power so as to provide a safer source of power. To accomplish this, the 12V input power signal 302 may first be decoupled via a series of capacitors C1, C2, C3 arranged in parallel of decreasing capacitance, then be channeled through a voltage regulator 306 designed to reduce the 12V signal 302 to a +5V signal 308. As part of this process, the voltage regulator 306 may reference the +5V signal 308 to a partly-unsafe field ground 310.

Following the voltage regulator 306, a series of capacitors C4, C5, C6 may be connected and configured to further clean and filter the power, thereby creating a lower DC voltage. This leads to the isolation DC-DC converter 208, as described above with reference to FIG. 2. As previously explained with reference to FIG. 2, the isolation DC-DC converter 208 may be configured to isolate the 5V signal 302 on the wall side B, from the patient side A. The resulting clean and safe voltage is a +VISO signal 312, referenced to a patient ground 314, a safe grounding reference.

Figure 4:
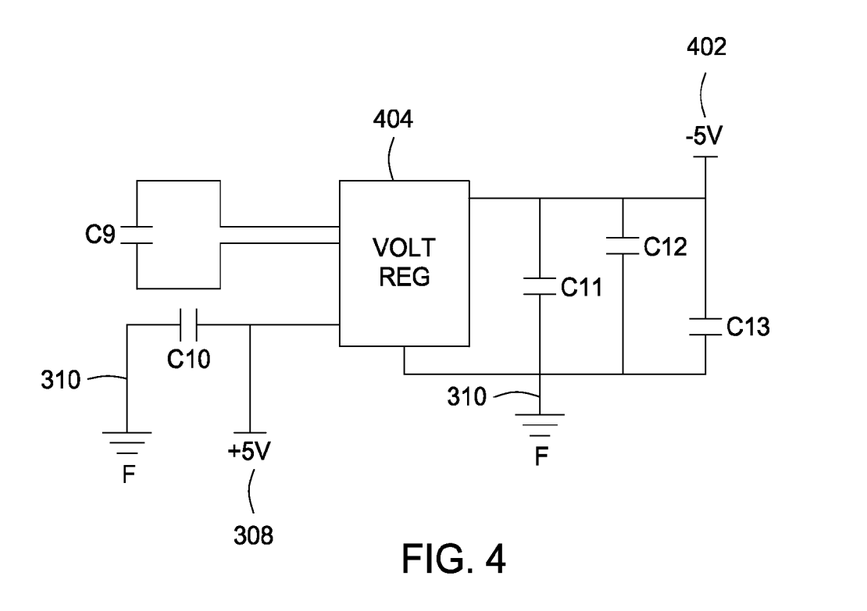
FIG. 4 illustrates a schematic diagram of a portion of the power distribution module disclosed in FIG. 2.

With reference to FIG. 4, the +5V signal 308 acquired in FIG. 3 may be converted into a −5V signal 402. The resulting signals 308, 402 may be used to power the circuitry located in the channels 210, 212, 214, 216 on the wall side B of the circuit board 114 (FIG. 2). In the illustrated embodiment, the +5V signal 308 is initially referenced to an unsafe field ground 310, but is subsequently filtered and amplified through a series of capacitors C9-C13 and a single voltage regulator 404. In an exemplary embodiment, the voltage regulator 404 may include a commercially-available LT1054 voltage regulator, available through TEXAS INSTRUMENTS®, or another similar device. The resulting −5V signal 402 may also be referenced to an unsafe field ground 310. The polar opposite signals may be required since amplifiers typically need dual-power supply signals to account for the positive and negative deflections to obtain the full sine wave. As will be seen below, the +5V signal 308 and the −5V signal 402 will be referenced by the several amplifiers located in the internal circuitry of each channel 210, 212, 214, 216 on the wall side B of the circuit board 114 (FIG. 2).

Figure 5:
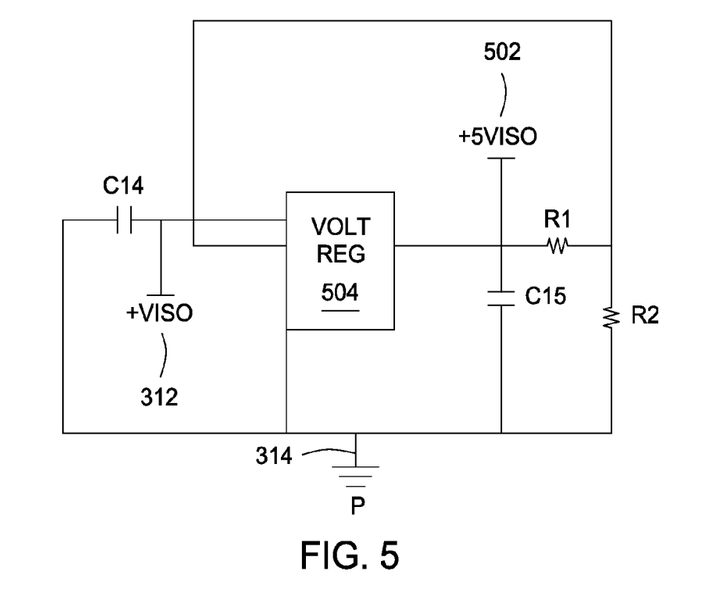
FIG. 5 illustrates a schematic diagram of a portion of the power distribution module disclosed in FIG. 2.

With reference to FIG. 5, the power distribution module 202 may be configured to use the clean +VISO 312 signal acquired in FIG. 3 and process it into a +5VISO 502 signal, a much cleaner signal including a very clean 5 volts of power. This may be accomplished, by filtering and amplifying the +VISO 312 signal through a series of capacitors C14, C15, a series of resistors R1, R2, and a voltage regulator 504. In at least one embodiment, the voltage regulator 504 may include the commercially-available LP2951 voltage regulator, available through NATIONAL SEMICONDUCTOR®. The resulting +5VISO 502 signal may be referenced to the very safe patient ground 314.

Figure 6:
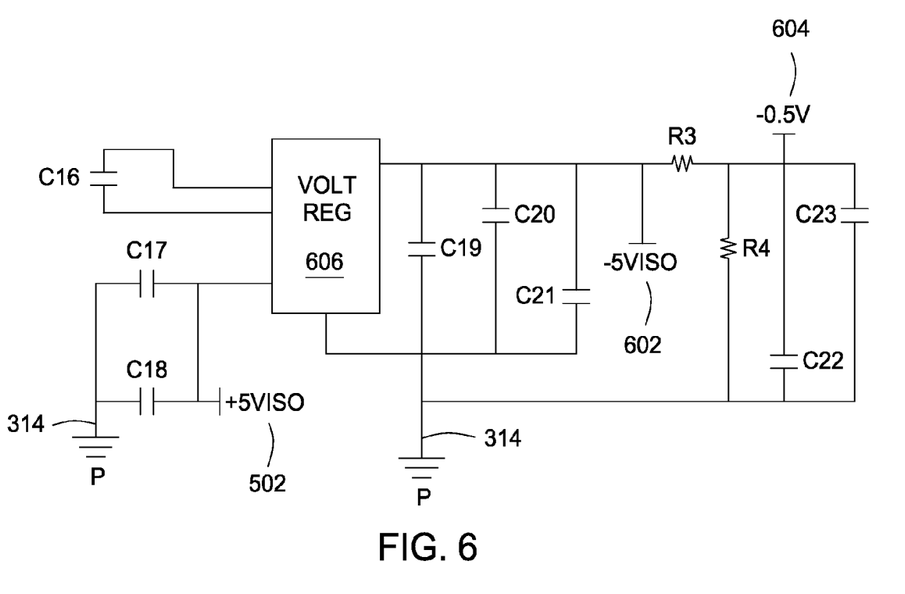
FIG. 6 illustrates a schematic diagram of a portion of the power distribution module disclosed in FIG. 2.

Lastly, with reference to FIG. 6, the power distribution module 202 may be configured to draw from the +5VISO 502 signal acquired in FIG. 5 above to create a −5VISO 602 signal and a −0.5V 604 signal. At the outset, the +5VISO 502 signal may be referenced to the safe patient ground 314. As illustrated in FIG. 6, the resulting signals 602, 604 may be created by filtering and amplifying the +5VISO 502 signal through a series of capacitors C16-C23, a series of resistors R3, R4, and a voltage regulator 606. In an exemplary embodiment, the voltage regulator 606 may include the commercially-available LT1054 voltage regulator, available through TEXAS INSTRUMENTS®. Moreover, the resulting −5VISO 602 signal and a −0.5V 604 signal may also both be referenced to the patient ground 314. As will be seen below, the +5VISO 502 signal and the −5VISO 602 signal will be referenced by the several amplifiers located in the internal circuitry of each channel 210, 212, 214, 216 on the patient side A of the circuit board 114 (FIG. 2).

Figures 7, 8:
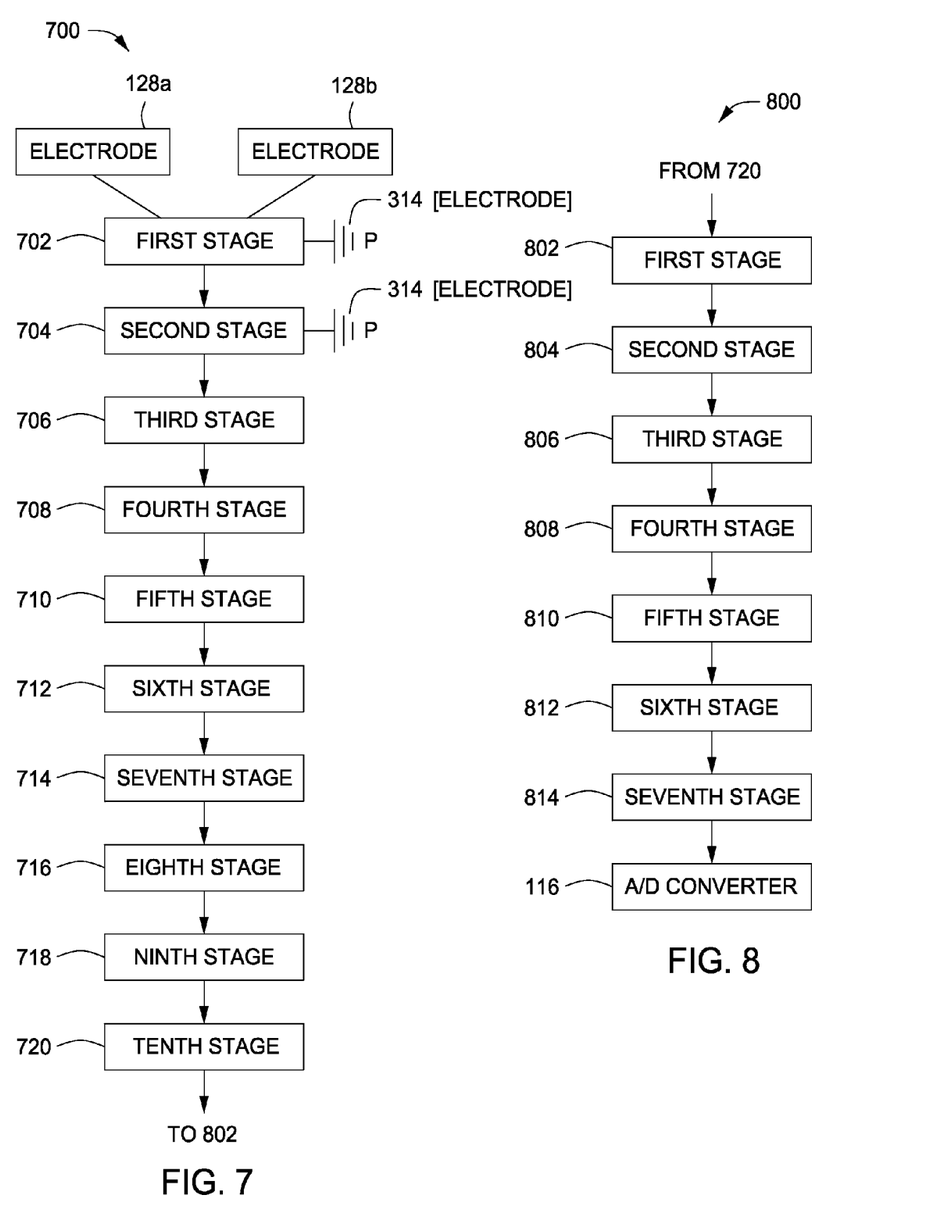
FIG. 7 illustrates a block circuit diagram of a portion of an embodiment of the circuit board disclosed in FIG. 2.
FIG. 8 illustrates a block circuit diagram of a portion of an embodiment of the circuit board disclosed in FIG. 2.

Referring now to FIG. 7, with continuing reference to FIG. 2, illustrated is a block diagram representative of the internal circuitry 700 located on the patient side A of the circuit board 114 for each channel 210, 212, 214, 216. As illustrated, the internal circuitry 700 may include several stages configured to receive and process a raw abdominal EMG signal from a patient. As will be appreciated, however, although the internal circuitry 700 of only one channel 210, 212, 214, 216 is herein described, the description may nonetheless apply to each channel 210, 212, 214, 216.

As explained above, each channel 210, 212, 214, 216 may be communicably coupled to a pair of electrodes 128a, 128b that are designed to acquire the raw abdominal EMG signals for processing. Specifically, the electrodes 128a,b may be configured to measure the differential muscle potential across the area between the two electrodes 128a,b and reference that potential to ground. As explained below, the electrodes 128a,b may also implement an impedance matching system that can provide relatively stable, impedance-independent output voltages to the internal circuitry 700. The first stage 702 may include an instrumentation amplifier configured to take the difference between the patient electrode voltages seen at electrodes 128a,b and reference that difference to a patient ground 314, which may take the form of an electrode. To support the instrumentation amplifier in obtaining the differential amplification, the first stage 702 may include an arrangement of several capacitors and resistors.

Also included in the first stage 702 may be a series of diodes configured as a safety feature to ground out the circuitry in the event an unexpected voltage spike is introduced via the electrodes 128a,b. A typical diode voltage drop is 0.7V, allowing the diode act as a switch that opens when voltage is increased or decreased by at least 0.7V. For example, in the event of a positive voltage spike, such as an emergency defibrillation of the patient where approximately 1,000V may course through the patient's body and potentially enter the electrodes 128a,b, a forward biased diode may be configured to shunt any positive voltage above the typical 0.7V drop that enters via the electrodes 128a,b to ground. Upon encountering the forward biased diode, the power spike may be channeled away from the circuit board 114 (FIG. 1) and to the power supply 112 (FIG. 1) which is medically-isolated to the wall outlet 108 (FIG. 1), as described above.

However, as is known in the art, every time there is a voltage spike, the voltage will tend to peak and oscillate between negative and positive while gradually decreasing its oscillation until it stabilizes. Therefore, to avoid sending an oppositely charged voltage spike back though the circuit board 114, or even to the patient through the electrode 128a,b, the circuitry in the first stage 702 may also include a reverse biased diode configured to absorb any negative voltage spikes exceeding the 0.7V drop in the negative direction. In an exemplary embodiment, a set of positive and negative diodes may be provided for each electrode 128a,b.

Moreover, the first stage 702 may include at least one pull-up resistor dedicated to each electrode 128a,b, since in some cases the patient is incapable of creating enough energy to register a valid abdominal EMG signal. Therefore, if needed, pull-up resistors may weakly pull or draw out the abdominal EMG signals from the patient.

The second stage 704 may be configured to provide further protection for the internal circuitry 700, and also further protect the patient from potentially dangerous leakage current traveling back through any electrodes 128a,b. In particular, the second stage 704 may include at least one resistor and a series of diodes, wherein the diodes may be designed to function similar to the diodes disclosed in the first stage 702 and further be referenced to a patient ground 314 designed to dissipate any stray excessive voltages. Therefore, the second stage 704 may serve as a failsafe mechanism in the event the diodes in the first stage 702 fail to completely absorb any unexpected peak voltages.

The third stage 706 and the sixth stage 712 may each include a high-pass filter, while the fourth stage 708 and the seventh stage 714 may each include a low pass filter. Throughout the hardware defined herein, the combination of high-pass and low-pass filters may be configured to amplify and filter the incoming abdominal EMG signals to frequencies broadly located between about 20 Hz to about 150 Hz, the typical frequency band of abdominal EMG activity found in humans. As can be appreciated, these filtration stages 706, 708, 712, 714 may eliminate some of the high or low frequency noises naturally emanating from the patient, or from the surrounding environment. In an alternative exemplary embodiment, the incoming abdominal EMG signals may be amplified and filtered to frequencies located between about 20 Hz to about 150 Hz by means of a single band-pass filter, thereby replacing the various filtration stages 706, 708, 712, 714 with a single band-pass filter stage.

The fifth stage 710 may include yet another voltage protection circuit, similar to the protection disclosed in stage three 706 above. In particular, the fifth stage 710 may provide a series of diodes and resistors configured to prevent the further influx of voltage surges, thereby protecting the internal circuitry 700 of the circuit board 114.

The eighth stage 716 may include a voltage divider configured to reduce the gain accumulated through the prior stages so as to provide the appropriate amount of voltage to the ninth stage 718. The ninth stage 718 may include a diode driver circuit having an operational amplifier ("op amp") configured to adjust a diode configuration that is designed to feed data and power to an optocoupler located in the tenth stage 720. In exemplary operation, the op amp may not have enough capacity to power an optocoupler. The diode configuration in the ninth stage 718, therefore, may compensate for the lack in voltage stemming from the op amp and be powered by +5VISO 502 (FIG. 5) and referenced to −5VISO 602 (FIG. 6). Alternatively, the diode configuration in the ninth stage 718 may compensate for an excess of voltage stemming from the op amp, and dissipate excess voltage safely to ground so as to not damage the ensuing optocoupler.

The tenth stage 720 may correspond to the linear optocoupler 218, as explained above with reference to FIG. 2. The linear optocoupler 218, also referred to as an optoisolator, may be configured to receive the partly-processed abdominal EMG signal from the internal circuitry 700 located on the patient side A and create an optical light signal that transmits across the optocoupler 218 to the wall side B. It should be noted that no electrical power is transferred over the linear optocoupler 218 from the patient side A to the wall side B. Instead, as explained above with reference to FIGS. 3 and 4, the wall side B is powered separately from the patient side A.

Referring now to FIG. 8, with continuing reference to FIG. 2, illustrated is a block diagram representative of the internal circuitry 800 located on the wall side B of the circuit board 114 for each channel 210, 212, 214, 216. As illustrated, the internal circuitry 800 may include several stages configured to receive the pre-processed abdominal EMG signal from patient side A and process that data for analog to digital (A/D) conversion.

The first stage 802 and the fifth stage 810 of the internal circuitry 800 may include a low-pass filter designed to filter the abdominal EMG signal from any outlying noises, thereby focusing the signal frequency to the broad frequency band lying between about 20 Hz to about 150 Hz. As can be appreciated, this frequency band may be filtered to a more narrow frequency band for more exact measurements.

The second stage 804 and the sixth stage 812 may each include a buffer amplifier. The buffer amplifiers provide electrical impedance transformation from one circuit to another. Specifically, each buffer amplifier may be configured to prevent the preceding stages from unacceptably loading the ensuing stages and thereby interfering with its desired operation.

The third stage 806 and the fourth stage 808 of the internal circuitry 800 may be configured as calibrating stages designed to refine the incoming EMG signals. In particular, each stage 806, 808 may include a low-pass filter defined by at least one capacitor and at least one resistor. However, the third stage 806 may include a tunable DC offset, configured to be tuned by the use of a localized potentiometer. Also, the fourth stage 808 may include a tunable gain, wherein the amplitude of the incoming EMG signal may be altered so as to acquire a known amplitude. Thus, a trained technician or the physician may be able to optimize the signal tuning at the hardware level. Although the frequency band may not be altered, the amplitude, gain, and DC offset may be manipulated to suit a particular application.

The seventh stage 814 may include a combination high-pass and low-pass filter configured to further filter the abdominal EMG signal from any outlying noises, thereby focusing the frequency to the broad frequency band lying between about 20 Hz to about 150 Hz.

The seventh stage 814 may include at least one 60 Hz notch filter configured to attenuate any noise generated by ambient lighting to a very low, unnoticeable level. As can be appreciated, to accommodate the varying frequencies outside of the U.S., the notch filter may be configured to filter a variety of frequencies. The signal leaving the seventh stage leads to the A/D converter 116 (FIG. 2) for digitizing. In an exemplary embodiment, the A/D converter may include a data acquisition ("DAQ") card, such as the commercially-available NI 6008, available through NATIONAL INSTRUMENTS®, as described above. Following the A/D converter, as explained above, the processed signal may be transmitted to the computer 104 (FIG. 1) for software manipulation and display.

The computer 104 may be configured to initiate the LABVIEW® software program, or other equivalent software programs, to acquire the digitized data and place it in an internal memory (not shown). The software may also be configured to algorithmically filter the incoming signal to remove any motion artifacts, or stray signals resulting from patient movement or someone contacting the electrodes 128 or leads and thereby causing a spike in signal activity. To accomplish this, the software may be programmed with an abdominal EMG threshold that automatically disregards registered signals that exceed frequencies lying outside of about 20 Hz to about 150 Hz. Alternative software data manipulation may include altering the gain of the signal, and calculating the root mean square of the data to obtain the signal representative of abdominal activity.

Contemplated in the disclosure, therefore, is hardware and software filtering of incoming abdominal EMG signals. Such multi-layer frequency filtering may have the advantageous effect of isolating only the signals representative of abdominal activity. After full signal processing has taken place in the computer 104, the processed data in the form of a signal representative of abdominal activity can be displayed, stored in memory for future reference, transmitted, or printed. As can be appreciated, a software program implemented by the computer 104 may be employed to execute instructions configured to carry out the process of presenting the signals representative of abdominal activity.

In another exemplary embodiment, the system 100, as generally described herein with reference to FIGS. 1-8, may also be used for acquiring and processing primary labor forces, or uterine contractions, before, during, and after delivery. Similar to the abdominal EMG signals, uterine contractions represent the electrophysiological activity in the muscle fiber of the uterus, and can be detected as a uterine EMG signal. Upon conception, uterine contractions commence and comprise coordinated contractions by individual myometrial cells of the uterus. These contractions are triggered by an action potential, and when electrodes are placed on the maternal abdomen, they may measure that action potential, thereby transmitting a raw uterine EMG signal.

In an exemplary embodiment configured to acquire and process uterine EMG signals, the signal processing module 102 and computer 104 may function substantially similar to the embodiments described above, except that uterine EMG signals, instead of abdominal EMG signals, are acquired and processed. As such, the signal processing module 102 and computer 104 will not be described again in detail.

To be able to acquire and process the uterine EMG signals, however, the combination of high-pass and low-pass filters in the system 100 must amplify and filter the incoming uterine EMG signals to frequencies broadly located between about 0.2 Hz to about 2 Hz, the typical frequency of uterine EMG activity found in humans. For example, referring to FIG. 7, the high pass filters of the third stage 706 and sixth stage 712, and the low pass filters of the fourth stage 708 and the seventh stage 714 may be configured to eliminate some of the high or low frequency noises naturally emanating from the patient by filtering the incoming uterine EMG signals to frequencies broadly located between about 0.2 Hz to about 2 Hz. Furthermore, with reference to FIG. 8, the low-pass filters of the first stage 802 and the fifth stage 810, and the combination high-pass and low-pass filter of the seventh stage 814 may be designed to further filter the uterine EMG signal from any outlying noises, thereby focusing the signal frequency even closer to the broad frequency band lying between about 0.2 Hz to about 2.0 Hz.

Additionally, the computer 104 may be configured to use the LABVIEW® software program to algorithmically filter the incoming signal to between about 0.3 Hz and about 1.0 Hz to thereby obtain a more precise signal representative of uterine activity. During the filtration process, software manipulation of the data may include removing any motion artifacts, or stray signals resulting from patient movement or someone contacting the electrodes 128 or leads and thereby causing a spike in signal activity. To accomplish this, the software may be programmed with a uterine EMG threshold that automatically disregards registered signals that exceed that limit. Alternative software data manipulation may include altering the gain of the signal, and calculating the root mean square of the data to obtain a signal representative of uterine activity.

The processed uterine EMG signals (primary labor force), representing the frequency and intensity of uterine contractions, may then be evaluated in conjunction with the processed abdominal EMG signals (secondary labor force), representing the intensity of abdominal contractions. As can be appreciated, an attending physician may be able to detect when a uterine contraction is transpiring and direct the maternal patient to push using the abdominal muscles to supplement the uterine contraction.

Furthermore, being able to view the intensity of the abdominal EMG signals may prove advantageous in cases where epidural anesthesia has diminished sensitivity to the abdominal muscles of a maternal patient. As is often the case, an anesthetized maternal patient may be unable to calculate the force of a voluntary abdominal contraction, or may be mistakenly pushing with muscles other than the abdomen. Such instances may prove counterproductive to the delivery process. Therefore, by viewing the abdominal EMG signals, an attending physician can regulate abdominal contraction and direct the maternal patient to increase the abdominal contraction intensity when necessary, thereby serving to advance the delivery process.

Regarding the electrodes 128 as described in FIGS. 1 and 2, they may further include a hardware-embedded software solution configured to continuously monitor the skin-to-electrode impedance. In monitoring the skin impedance, the electrodes 128 may be configured to alter the input impedance of the monitoring circuitry to dynamically adapt to the changing impedance mismatch between the patient skin and the electronics in the signal processing module 102. In at least one embodiment, the skin-to-electrode impedance may be implemented in a continuous-monitoring mode or time-defined monitoring mode, to allow either real-time implementation of the impedance matching or predefined matching based upon the accuracy required by the medical procedure.

In an exemplary embodiment, the skin-to-electrode impedance matching may be accomplished via the methods and systems described in co-pending U.S. application Ser. No. 12/758,552, entitled "Method and Apparatus to Determine Impedance Variations in a Skin/Electrode Interface," the contents of which are incorporated herein by reference in their entirety. In another exemplary embodiment, the skin-to-electrode impedance matching may be accomplished as described below.

Figure 9:
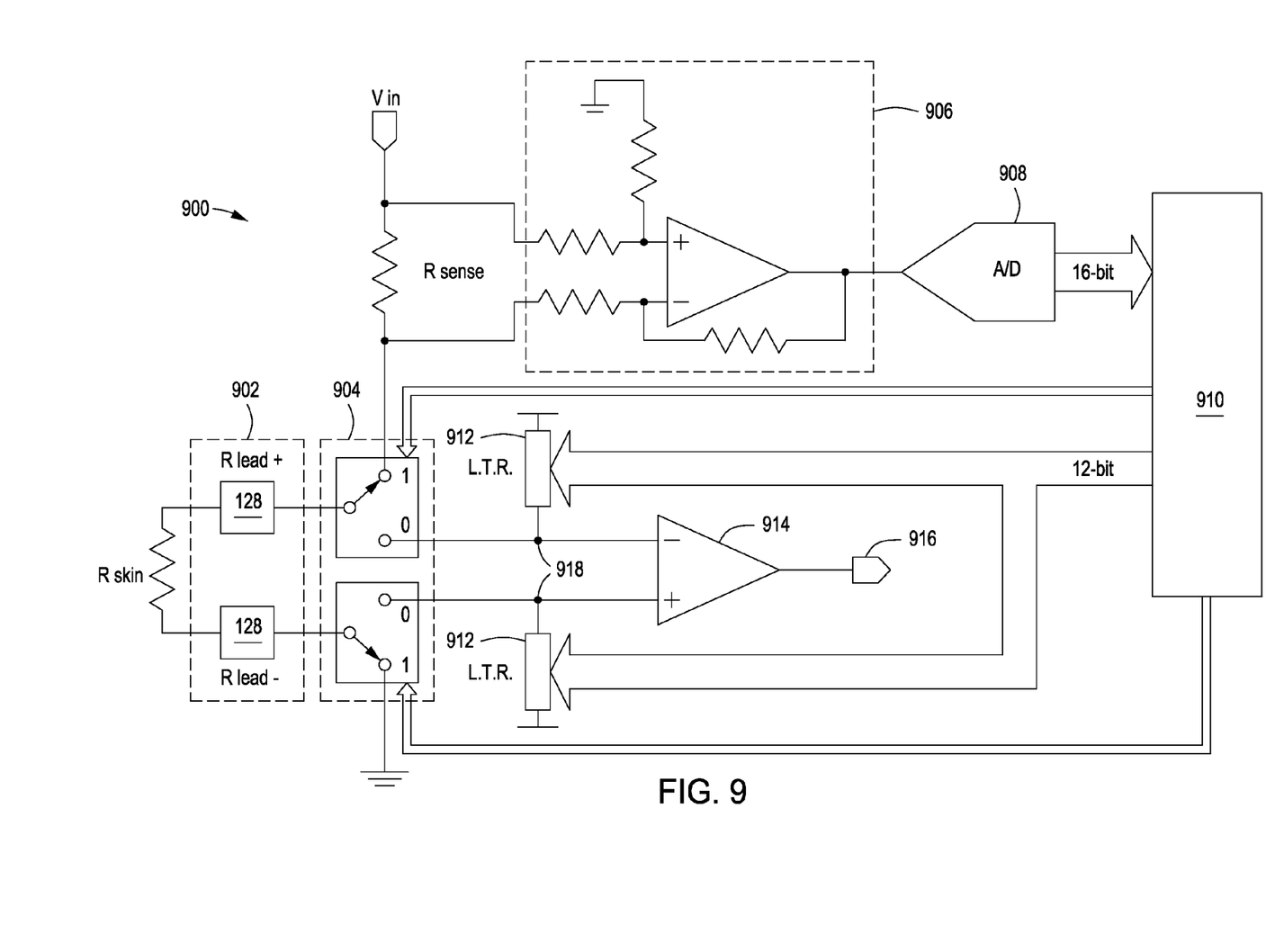
FIG. 9 illustrates an exemplary schematic electrical circuit for a skin impedance matching system, according to at least one embodiment of the present disclosure.

FIG. 9 illustrates an exemplary schematic electrical circuit for a skin impedance matching system 900. The system 900 may be configured to measure the skin-to-electrode impedance and adaptively alter the input impedance of the electrical monitoring circuitry to match the measured skin-to-electrode impedance. The system 900 may include a first matching module, or measurement circuit, having a skin-to-electrode interface 902 including electrodes 128, a pair of switches 904, a current sensing differential amplifier 906, an A/D converter 908, and a microprocessor 910.

In exemplary operation, the measurement circuit senses the input impedance of the skin-to-electrode interface, amplifies, digitizes, and provides information to the microprocessor 910. Within the microprocessor 910, an embedded software routine may be configured to analyze the incoming data and generate a series of control signals to a communicably coupled resistor ladder network 912. In at least one embodiment, the control signals are 12-bit communications.

Following the resistor ladder network 912 may be a second sensing module or mode, a differential amplifier 914 may be employed to amplify the incoming electrical signals generated by the patient. In an exemplary embodiment, a medical device 916, such as the signal processing module 102 (FIG. 1), may be attached to the amplifier 914 in order to obtain data from the electrodes 128. As can be appreciated, multiple circuits may be progressively switched using the same electrodes 128, if appropriate. In at least one embodiment, the amplifier 914 is not employed. In alternative embodiments, the amplifier 914 may be integrally-embodied in the medical device 916.

Figure 10:
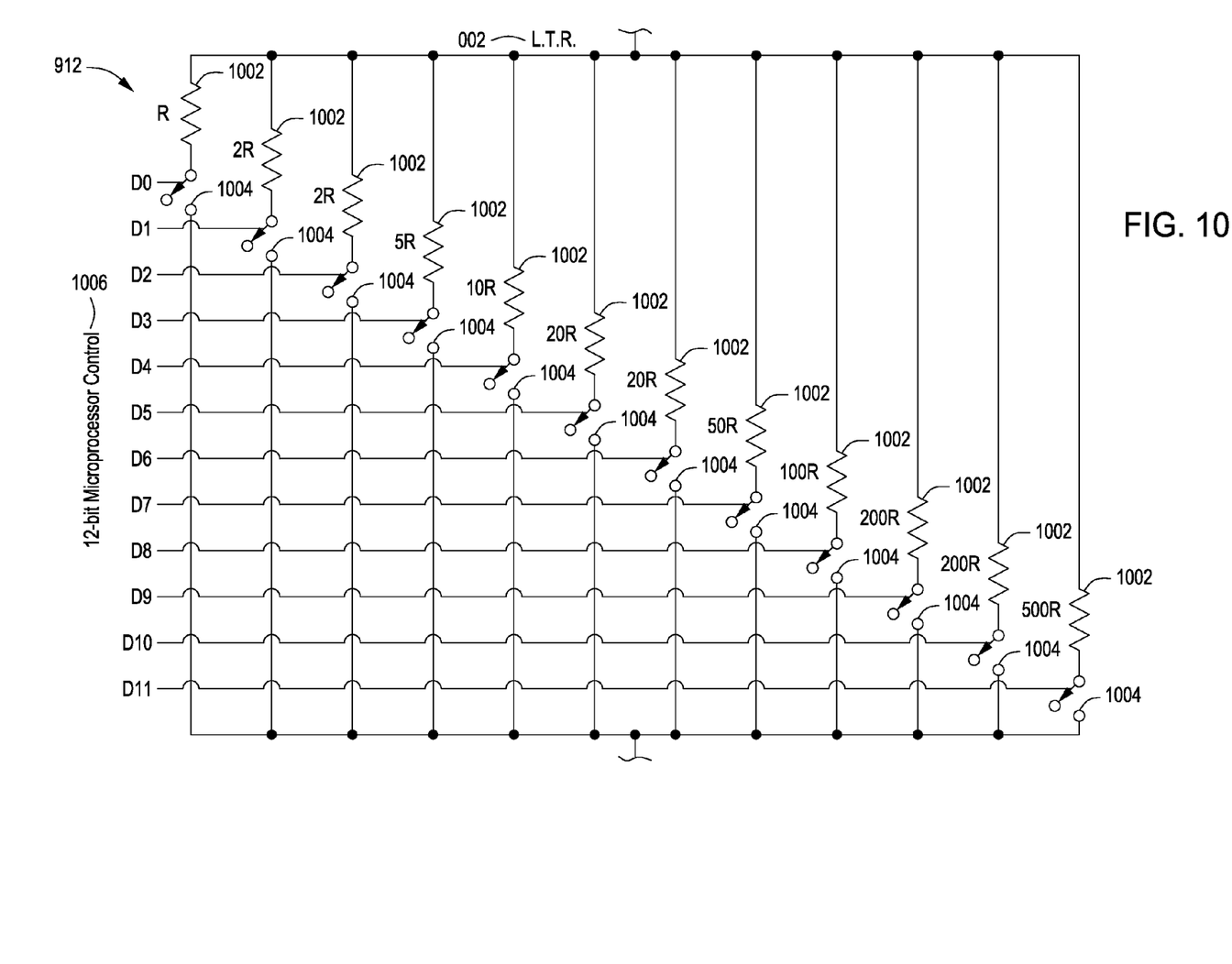
FIG. 10 illustrates an exemplary electrical schematic of a resistor ladder network, according to at least one embodiment of the present disclosure.

Referring now to FIG. 10, illustrated is an exemplary electrical schematic of at least one resistor ladder network 912. As shown, the resistor ladder network 912 may include a plurality of resistors 1002 and microcontroller-activated switches 1004 to implement a number of resistor 1002 combinations in parallel, thereby allowing tremendous accuracy in the total impedance generated by the combined resistor ladder 912. Depending on the application, the resistor 1002 values may vary. For example, in the illustrated exemplary embodiment, R may equal 1K Ohms, where the value of R may vary per application.

In exemplary operation, with continuing reference to FIGS. 9 and 10, the electrodes 128 communicably coupled to the electronic monitoring system 900 may first be placed on the patient skin surface. The microprocessor 910 may then be configured to adjust the switches 904 to the "ON" or 1 position, thereby creating a current flow path from Vin, through Rsense, Rlead+, Rskin, Rlead− to ground. In an exemplary embodiment, the microprocessor 910 may communicate to the switches 904 with 2-bit, or even 1-bit, signals. The voltage drop, and thus the current through the resistor Rsense, may then be measured and amplified by the current-sensing differential amplifier 906. The resulting analog signal may then be digitized by the A/D converter 908 and passed in a multi-bit format to the microprocessor 910. An embedded-software routine in the microprocessor 910 may be configured to analyze the digitized information and thereby calculate the resistive load applied by the skin-to-electrode interface 902.

The microprocessor 910 may then create a set of control signals 1006 (FIG. 10) and send them to the resistor ladder network 912 in order to activate the switches 1004 as needed. Activating the switches 1004 may include creating a set of parallel resistors 1002 configured to generate an overall resistive load corresponding to the resistive load created by the skin-to-electrode interface 902. Upon completion of the resistive-matching operation, the microprocessor 910 may then set the input switches 904 back to the "OFF" or 0 position, thereby returning the electronic system 900 to regular operation as a medical monitoring device, while leaving the resistor ladder network 912 programmed to match the skin-to-electrode impedance.

The exemplary values of resistors 1002 disclosed in FIG. 2 may be configured to generate a variety of resistance values by various combinations of switches 1004 that are no more than a 5% variance with any skin impedance generally between 10K ohms to 100K ohms. Due to the matching operation, the voltage from monitoring the skin through the electrodes 128 may be split at the junctions 918 where a portion of the voltage flows through the network 912 and the other portion flows through the amplifier 914.

The foregoing has outlined features of several embodiments so that those skilled in the art may better understand the detailed description that follows. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions and alterations herein without departing from the spirit and scope of the disclosure.

What is claimed is:

1. A system for processing abdominal EMG signals, comprising:
a signal processing module having an internal processing circuit;
a plurality of pairs of skin impedance electrodes communicably coupled to the signal processing module and configured to acquire and transmit a raw abdominal EMG signal from a patient to the internal processing circuit where the raw abdominal EMG signal is amplified and filtered to a frequency band between about 20 Hz and about 150 Hz, thereby obtaining a processed abdominal EMG signal, wherein said skin impedance electrodes further comprise a skin-to-electrode impedance matching system for monitoring a plurality of skin-to-electrode impedances and altering the input impedance of said processing circuit to adapt to said skin-to-electrode impedances;
an analog to digital converter operatively coupled to the processing circuit and configured to convert the processed abdominal EMG signal into a digital abdominal EMG signal; and
a computer communicably coupled to the signal processing module and configured to receive and process the digital abdominal EMG signal into a viewable signal representative of abdominal activity, whereby an intensity of abdominal activity can be evaluated alongside a uterine EMG signal.

2. The system of claim 1, wherein the computer has a wireless receiver and the signal processing module further comprises a wireless transmitter for wirelessly transmitting the digital abdominal EMG signal to the wireless receiver of the computer.

3. The system of claim 1, wherein the signal processing module further comprises a circuit board having a patient side and a wall side, the patient side being separated from the wall side by an isolation DC-DC converter configured to isolate power signals and prevent stray charges from crossing over from the wall side to the patient side or from the patient side to the wall side.

4. The system of claim 3, wherein the circuit board further comprises a plurality of channels extending across the patient side to the wall side, each channel being separated by an optocoupler configured to prevent potential electrical damage to the circuit board or the patient.

5. The system of claim 1, wherein the computer processes the digital abdominal EMG signal by removing motion artifacts from the processed EMG signal.

6. The system of claim 1, wherein the software is configured to determine the root mean square of the digital abdominal EMG signal to obtain the signal representative of abdominal activity.

7. The system of claim 6, wherein the signal representative of abdominal activity is displayed on a monitor.

8. The system of claim 1, wherein the signal processing module further comprises:
a matching module configured to determine the skin impedance of the patient by sensing an input impedance from the patient through the plurality of pairs of skin impedance electrodes, and amplifying and digitizing the input impedance;
a resistor ladder network configured to match the skin impedance using at least one resistor;
a microprocessor configured to analyze the input impedance and generate a series of control signals to direct the resistor ladder network to match the skin impedance; and a sensing module configured to sense uterine EMG signals from the patient through the plurality of pairs of skin impedance electrodes in conjunction with the resistor ladder network.

9. The system of claim 8, wherein the sensing module is communicably coupled to the signal processing module.

10. A method of processing abdominal EMG signals, comprising:
obtaining a raw analog abdominal EMG signal from of plurality of pairs of skin impedance electrodes applied to a maternal abdomen of a patient;
monitoring a plurality of skin-to-electrode impedances and altering the input impedance of the monitoring circuitry to adapt to said skin-to-electrode impedances;
processing the raw analog abdominal EMG signal in a signal processing module by amplifying and filtering the raw analog abdominal EMG signal to a frequency band between about 20 Hz and about 150 Hz, thereby obtaining a processed analog signal;
converting the processed analog signal to a digital abdominal EMG signal; and
converting the digital abdominal EMG signal into a signal representative of abdominal activity using a computer communicably coupled to the signal processing module.

11. The method of claim 10, further comprising evaluating the signal representative of abdominal activity in conjunction with a signal representative of uterine activity in order to coincide abdominal activity with uterine activity.

12. The method of claim 10, further comprising matching a skin impedance of the patient with an impedance of the pair of electrodes.

13. The method of claim 12, wherein matching the skin impedance of the patient comprises:
determining the skin impedance of the patient by sensing an input impedance from the patient, and amplifying and digitizing the input impedance to obtain a processed input impedance;
analyzing the processed input impedance using a microprocessor;
generating a control signal to direct a resistor ladder network to match the skin impedance;
matching the skin impedance using at least one resistor in the resistor ladder network; and
sensing the raw analog abdominal EMG signals from the patient through a sensing module coupled to pair of electrodes in conjunction with the resistor ladder network.

14. The method of claim 13, wherein the sensing module is communicably coupled to the signal processing module.

15. The method of claim 10, wherein converting the digital abdominal EMG signal into a signal representative of abdominal activity using a computer comprises:
removing motion artifacts from the digital abdominal EMG signal; and
determining the root mean square of the digital abdominal EMG signal.

16. The method of claim 15, wherein the signal representative of abdominal activity and the signal representative of uterine activity are jointly displayed on a monitor coupled to the computer.

17. The method of claim 10, wherein the signal processing module has a circuit board having a patient side and a wall side, the patient side being separated from the wall side by a isolation DC-DC converter configured to isolate power signals and prevent stray charges from crossing over from the wall side to the patient side or from the patient side to the wall side.

18. The method of claim 17, wherein the circuit board further comprises a plurality of channels extending across the patient side to the wall side, wherein the plurality of channels are separated by an optocoupler configured to prevent potential electrical damage to the circuit board and the patient.

19. A computer program for processing abdominal EMG signals from a patient, the computer program product comprising:
a computer-readable medium, that when executed by a processor, is configured to control a method for processing abdominal EMG signals from a patient, the computer readable medium having computer usable program code embodied therewith, the computer usable program code comprising program instructions operable for:
obtaining a raw analog abdominal EMG signal from at least a plurality of pairs of skin impedance electrodes coupled to a maternal abdomen of a patient;
monitoring a plurality of skin-to-electrode impedances and altering the input impedance of the monitoring circuitry to adapt to said skin-to-electrode impedances;
processing the raw analog abdominal EMG signal in a signal processing module to amplify and filter the raw analog abdominal EMG signal to a frequency band between about 20 Hz and about 150 Hz to obtain an amplified and filtered analog signal;
converting the amplified and filtered analog signal to a digital abdominal EMG signal;
transmitting the digital abdominal EMG signal to a computer;
processing the digital abdominal EMG signal in the computer to obtain a signal representative of abdominal activity; and
displaying the signal representative of abdominal activity on a monitor communicably coupled to the computer, whereby an intensity of abdominal activity can be evaluated alongside a uterine EMG signal.

20. The computer program of claim 19, wherein processing the digital abdominal EMG signal in the computer further comprises:
removing motion artifacts from the digital abdominal EMG signal; and
determining the root mean square of the digital abdominal EMG signal.

* * * * *